(12) United States Patent
Mitchell et al.

(10) Patent No.: US 9,182,381 B2
(45) Date of Patent: Nov. 10, 2015

(54) APPARATUS AND METHODS FOR MEASURING CONCENTRATIONS

(71) Applicant: Meggitt Safety Systems, Inc., Simi Valley, CA (US)

(72) Inventors: Mark D. Mitchell, Simi Valley, CA (US); Kurt E. Mills, Simi Valley, CA (US); John Forbes Black, Simi Valley, CA (US)

(73) Assignee: Meggitt Safety Systems, Inc., Simi Valley, CA (US)

( * ) Notice: Subject to any disclaimer, the term of this patent is extended or adjusted under 35 U.S.C. 154(b) by 0 days.

(21) Appl. No.: 13/843,212

(22) Filed: Mar. 15, 2013

(65) Prior Publication Data

US 2014/0260530 A1   Sep. 18, 2014

(51) Int. Cl.
*G01N 33/00* (2006.01)
*G01N 25/18* (2006.01)

(52) U.S. Cl.
CPC ............ *G01N 33/0027* (2013.01); *G01N 25/18* (2013.01)

(58) Field of Classification Search
CPC .................................................. G01N 33/0027
See application file for complete search history.

(56) References Cited

U.S. PATENT DOCUMENTS

| 2,586,899 | A | | 2/1952 | Yanikoski |
| 3,784,902 | A | * | 1/1974 | Huber ........................ 73/863.03 |
| 5,150,577 | A | | 9/1992 | Mitchell et al. |
| 5,623,833 | A | | 4/1997 | Mitchell et al. |
| 5,688,324 | A | * | 11/1997 | Umaba ........................ 118/401 |
| 6,021,678 | A | * | 2/2000 | Vardiman et al. .......... 73/863.11 |
| 8,161,790 | B2 | | 4/2012 | Ayers |
| 2009/0326279 | A1 | * | 12/2009 | Tonkovich et al. ............ 568/487 |
| 2011/0056273 | A1 | * | 3/2011 | Gorbunov et al. ........... 73/28.01 |

OTHER PUBLICATIONS

Pitts, William M., *Species Concentration Measurements*, In: Yang, J.C., et al., Editors, Solid Propellant Gas Generators: Proceedings of the 1995 Workshop, NISTIR 5766, Jun. 28-29, 1995, 147-172, pp.
Braun, Emil, et al., *Determination of Suppression Concentration for Clean Agents Exposed to a Continuously-Energized Heated Metal Surface*, National Institute of Standards and Technology, Halon Options Technical Working Conference, May 6-8, 1997, 149-161 pp.
Pitts, William M., et al., *11. Real-Time Suppressant Concentration Measurement*, In: Gann, R.G., Editor, Fire Suppression System Performance of Alternative Agents in Aircraft Engine and Dry Bay Labaotry Simulations, vol. 2, Section 11, NIST SP 890, 319-590 pp, 1995.

* cited by examiner

*Primary Examiner* — Laura Martin
*Assistant Examiner* — Alex Devito
(74) *Attorney, Agent, or Firm* — Dickstein Shapiro LLP (57) ABSTRACT

A probe for measuring an agent in gas and liquid form comprising: a body including an inner chamber and comprised of a porous material; and a heating element in thermal communication with the porous material.

22 Claims, 7 Drawing Sheets

```
                          ┌──────────────────────┐
                          │   Heating a porous   │
              202 ────────│     material         │
                          │     of a probe       │
                          └──────────┬───────────┘
                                     │
                                     ▼
                          ┌──────────────────────┐
                          │ Measuring an air flow│
              204 ────────│  velocity proximate  │
                          │     to the probe     │
                          └──────────┬───────────┘
                                     │
                                     ▼
                          ┌──────────────────────┐
                          │ Measuring an air     │
              206 ────────│ temperature proximate│
                          │     to the probe     │
                          └──────────┬───────────┘
                                     │
                                     ▼
                          ┌──────────────────────┐
                          │ Adjusting the amount │
                          │ of heat provided to  │
                          │    the porous        │
              208 ────────│  material based on   │
                          │ the measured air     │
                          │ temperature to       │
                          │ facilitate vaporiza- │
                          │ tion of a liquid     │
                          │     phase agent      │
                          └──────────────────────┘
```

APPARATUS AND METHODS FOR MEASURING CONCENTRATIONS

The present patent document relates to probes and sensors. More particularly, the present patent document relates to probes, sensors and methods for measuring concentrations of materials that do not fully vaporize and therefore, exist in a gas liquid mixture.

BACKGROUND

Aircraft operating conditions provide unique challenges for the design of aircraft fire suppression systems. For example, aircraft fire suppression systems must work at a wide range of temperatures. The limits of these temperature ranges may extend from +105° C. when the aircraft is on the tarmac on a hot day, to as low as −55° C. when the aircraft is at high altitudes.

For more than 50 years Halon 1301 has been the agent of choice for aircraft engine and APU fire suppression applications. Halon 1301 has specific desirable properties that facilitate distribution of the agent throughout all areas of the fire zone. The low boiling point of Halon 1301 and the material's ability to freely vaporize at each outlet or discharge location in the distribution system, even in harsh environments, are desirable physical properties. Halon 1301 is typically stored in a pressurized bottle, using nitrogen as the pressurizing gas. Upon discharge, the agent freely vaporizes, changing state from a liquid phase to a gas phase and completely mixing with air.

Aircraft fire suppression systems are designed based on the agent weight, traditionally Halon 1301, required to achieve a specific minimum agent concentration in the fire zone immediately after agent discharge. In order for a fire suppression system to obtain aircraft certification, the system must demonstrate the ability to achieve a minimum specified agent concentration within the subject fire zone. A certification test is typically performed by discharging the fire extinguisher bottle and measuring the agent concentration in the fire zone during aircraft operation, either in flight or on the ground.

Agent concentration is measured by sampling the air in the fire zone and measuring the concentration of the Halon vapor within the sampled air. During a typical aircraft fire suppression system test, approximately twelve (12) probes of small tubing are placed at designated locations within the fire zone. The opposite end of each probe is connected to the measuring instrument. Different measuring instruments or sensors may be used depending on the particular fire suppression agent that is being used. The Halonyzer is an example of a well-known measuring instrument. A pump in the measuring instrument is used to draw a steady stream of air from the fire zone, through each probe, and into a sensor. Output from the sensor indicates the concentration of Halon gas relative to air. The relative measurement indication is converted to a volumetric concentration value.

The Halonyzer instrument and the 24-channel CME (concentration measurement instrument) are presently only capable of measuring the concentration of gas phase fire suppression agents relative to air. Halon concentrations within the sampled air may be measured using standard sample probe techniques because the Halon completely vaporizes in the air.

Environmental concerns over ozone depletion due to Halon 1301 have resulted in "green" activity to identify possible fire suppressing agent replacements for Halon 1301. Many of the agents that are potential "green" replacements for Halon 1301 have a higher boiling point than Halon 1301. Any potential agent that has a boiling point higher than the temperature in the fire zone when discharged will not freely vaporize, i.e. change state spontaneously from liquid to gas upon discharge. Upon discharge at low temperatures, many of the potential replacements for Halon 1301 exist as a "fog mist" because of their higher boiling points. The "fog mist" is a mixture of agent vapor (gas phase) and small liquid phase drops. An accurate and repeatable concentration measurement of these "fog mists" is not possible using current gas probe measurement techniques. The liquid phase drops do not mix homogeneously with air and the drops stick to the sides of the sample tubes due to surface tension. The cohesive nature of the very small droplets in the "fog mist" and adhesive nature of the drops onto current sample tubing are problematic. No probe design or instrument is currently available to perform accurate and repeatable post-discharge measurements for indicating real-time volumetric or mass concentration values of agents that exist in both the gas and liquid form.

SUMMARY

In view of the foregoing, an object according to one aspect of the present patent document is to provide a probe for measuring the concentration of an agent that exists in both the liquid and gas phase within a volume, and more particularly, to provide a probe for measuring the concentration of fire suppressant mixtures that exist in both the liquid and gas phase after discharge. In other aspects of the present patent document, methods and systems related thereto are provided. Preferably, the provided methods, systems and mixtures address or at least ameliorate one or more of the problems described above. To this end, a probe for use in measuring an agent in gas and liquid form is provided. In one embodiment the probe comprises: a body including an inner chamber and comprising a porous material; and a heating element in thermal communication with the porous material. The porous material defines a plurality of gas passageways in communication with the inner chamber on one end and atmosphere on the other end. The heating element is preferably designed to be able to heat the porous material sufficiently to vaporize the liquid phase of any agent coming in contact with the porous material before passing through the body.

In some embodiments, the probe further comprises a thermal sensor located proximate to the inlet and designed to measure an air temperature. In some of the embodiments that include a thermal sensor, the thermal sensor may be located within the porous material. In the embodiments that include a thermal sensor, the temperature readings from the thermal sensor may be used to control the heating element and optimize vaporization of the agent without overheating.

In some embodiments, the probe further comprises an anemometer located proximate to the inlet and designed to measure an air velocity, for example, through the porous material. As a result, in some of the embodiments that include an anemometer, the anemometer may be located within the porous material. In a preferred embodiment, the anemometer is a hot-wire anemometer; however, other types of anemometers may be used in other embodiments.

In some embodiments of the probes disclosed herein, the porous material has a unique geometry to facilitate vaporization of the agent. For example, the porous material may be made from a sintered powder material to allow the efficient manufacture of unique and complex geometries. In other embodiments, other materials or manufacturing processes may be used. In some embodiments, the unique geometries may comprise a plurality of convoluted paths that define a plurality of tortuous gas passageways extending from the exterior surface of the probe body (or atmosphere) to the inner chamber of the probe body. Preferably the plurality of gas passageways are sufficiently small to prevent the liquid phase of any agent landing on the porous material from passing through the probe body without first being vaporized.

In various different embodiments, the components of the probe may be located in various different locations. In some embodiments, the heating element, the anemometer, and the thermal sensor may each be located within the porous material. In other embodiments, a subset of the heating element, the anemometer, and the thermal sensor maybe located in the porous material.

In yet another aspect of the embodiments of a probe disclosed herein, a probe for use in measuring an agent in gas and liquid form is provided. In at least one embodiment, the probe comprises: a probe body comprising a porous material; a thermal sensor located within the porous material; and an anemometer located within the porous material. The porous material defines a plurality of gas passageways, preferably tortuous gas passageways, sized to permit the agent in the gas phase to pass there through while substantially blocking the agent while in the liquid phase from passing through.

In some of those embodiments, the probe may further comprise a heating element in thermal communication with the porous material.

In some embodiments of the probe, the heating element is located within the porous material. Placing the heating element within the porous material can make controlling the temperature of the porous material more efficient and provide a faster response.

In another aspect of the patent document, a probe and sensor system is provided. In one embodiment, the probe and sensor assembly comprises: a probe having the structure of any of the probes discussed in the various embodiments above and a gas sensor in gas communication with the plurality of gas passageways in the porous material. In one embodiment, the gas sensor is in gas communication with the gas passageways in the porous material via a conduit interposed between the probe and gas sensor. In yet other embodiments, at least a portion of the conduit may be thermally conditioned by a thermal conditioning element. The thermal conditioning element may be active or passive and is preferably designed to prevent condensation of the agent as it passes from the probe to the sensor.

In preferred embodiments, the probe and sensor system is designed to measure discharged fire retardants. Such fire retardants may include "green" substitutes for Halon 1301, such as Novec 1230 and $CF_3I$ (Triodide®) to name a few.

In another aspect of the embodiments disclosed herein, a method of measuring the concentration of an agent in gas and liquid form is provided. One embodiment of the method comprises the steps of: heating a probe comprising a porous material; measuring an air temperature proximate to the probe; and adjusting the heat added in the heating step based on the measured air temperature in order to facilitate vaporization of a liquid phase agent.

In a preferred embodiment, the method further includes the step of measuring the air velocity proximate to the probe. In the embodiments that measure the air velocity, the mass flow rate of the agent may be calculated using the measured air velocity. Once the mass flow rate is calculated, the concentration of the agent maybe calculated in a further step.

The preferred embodiments of the methods disclosed herein may be used in operation to detect fire retardants. In some embodiments, those fire retardants may be "green" substitutions for Halon 1301.

As described more fully below, the probes, probe and sensor assemblies, and methods of use are novel embodiments for measuring the concentrations of agents that exist in both the liquid and gas phases and in particular fire suppressants that exist in both the liquid and gas phases when discharged. These probes, probe and sensor assemblies, and methods may be particularly suited for measuring the discharge of fire retardants in cold temperature environments, such as those found in aircraft. Further aspects, objects, desirable features, and advantages of the probes, probe sensor systems and methods disclosed herein will be better understood from the detailed description and drawings that follow in which various embodiments are illustrated by way of example. It is to be expressly understood, however, that the drawings are for the purpose of illustration only and are not intended as a definition of the limits of the claimed invention.

DETAILED DESCRIPTION OF THE EMBODIMENTS

Recently it has been discovered that organic materials such as FK-5-1-12, dodecafluoro-2-methylpentan-one, $CF_3I$, compounds similar to or derived from FK-5-1-12 and $CF_3I$, large, high molecular weight organic molecules containing a halogen with a boiling point temperature below that of FK-5-1-12, HFC-125, and other organics may be used as fire suppressants, retardants, or extinguishers (hereinafter "Halon Replacements"). These compounds are more environmentally friendly than Halon 1301. In particular, Halon Replacements are significantly less harmful to the ozone layer than Halon 1301. However, the boiling points of the Halon Replacements are higher than Halon 1301 and these compounds do not completely vaporize in the low temperature environments found on aircraft.

By using an organic blend of compounds that comprises component compounds, it is possible to create a mixture that retains desirable characteristics of each of its components. Accordingly, fire suppressing agents may be formed that have numerous desirable features of their components and are thus better suited to handle fire suppression in diverse environments like the ones found on aircraft. Organic compounds may be mixed with the Halon Replacements to lower the boiling points as discussed in U.S. patent application Ser. No. 13/423,133 and titled "Fire Suppressing Materials and Systems and Methods of Use," which is herein incorporated by reference in its entirety. However, even after mixing a Halon Replacement with other compounds to form a mixture with a lower boiling point, the resultant mixture may still not completely vaporize in the low temperature environments an aircraft may experience, particularly at altitude.

The present patent document teaches the use of a unique and innovative probe and sensor assembly in order to measure the concentration and distribution of materials that exist in both a gas and liquid "fog mist" state and the methods associated with those measurements. In the preferred embodiment, an innovative probe and sensor assembly is disclosed that is designed to measure the discharge concentration of Novec 1230 and/or CF3I (Triodide®) in low temperature air. The embodiments of the probe and sensor assembly described herein may be used to more accurately indicate the concentration of high boiling point agents in air and reflect a more accurate mass measurement reference of Novec 1230 and/or $CF_3I$ (Triodide®) in low temperature air by using an appropriate probe and sensor. Measurements of this type are crucial for the approval of these new fire suppressants as acceptable solutions to aircraft fire control and potential replacements for Halon 1301.

As used herein the term "agent" means any substance that may exert some force or effect. An agent may refer to any material, compound or chemical. The term agent is used to refer to the material, compound or chemical that is present in a volume and for which a concentration is being measured and/or calculated. As just one example, fire retardants such as Novec 1230 are considered an "agent" with respect to the present patent document.

As used herein the term "air" is used to refer to the gases or gas present in a volume that is not part of the agent. "Air," as used herein, does not have to be made of any particular composition of gases such as those typically found in Earth's atmosphere. "Air" includes any composition of gases and may also be a partial vacuum or vacuum in which very few molecules of gas exist.

As used herein the term "volume" means the magnitude of the three-dimensional space enclosed within or occupied by an object. In particular, volume is used to refer to the magnitude of any three-dimensional space in which an agent is disseminated.

In a number of places in the present patent document sensors or heating elements are said to exist within another element. With respect to the use of "within" as used in relation to the location of any sensors or heating elements, "within" means that at least a portion of the sensor or heating element is within the other element. It is not necessary for the entire sensor or heating element to be inside the other element for it to be located "within." As just one example, a portion of the sensor or heating element may be located inside the element and the electric leads corresponding to such sensor and heating element may be located outside the element and the sensors and/or heating element may still be considered "within" the other element.

While the above description of the existing problems in the art is expressed in terms of solving a particular need for measuring the discharge of a fire suppressant in an aircraft, the applications of the embodiments described herein are not limited to any field and are equally applicable to the measurement of any agent or material that exists in a gas/liquid "fog mist" form.

Figure 1:
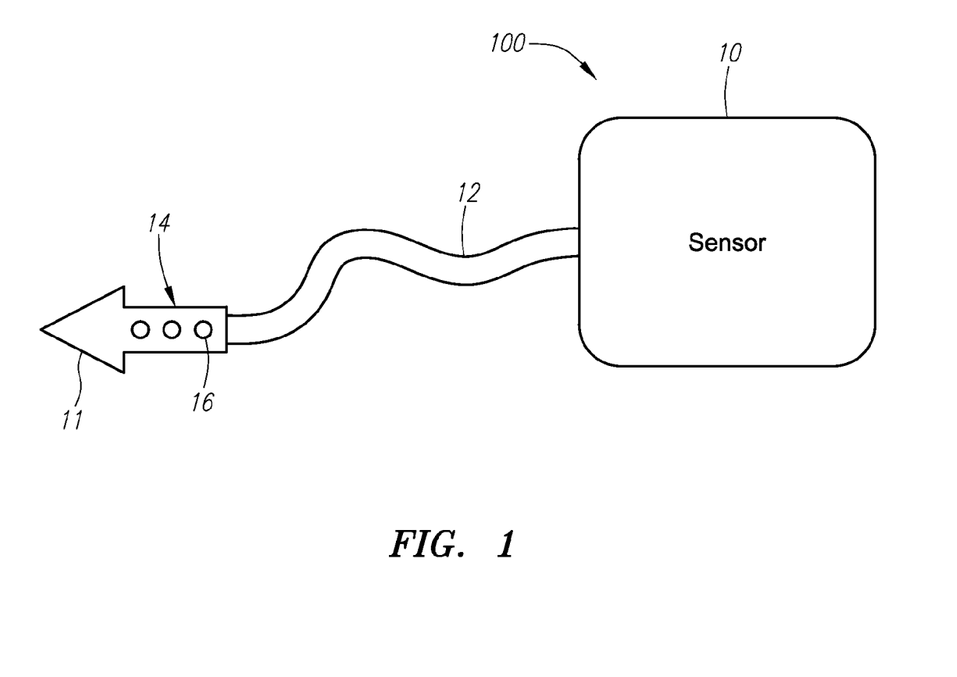
FIG. 1 illustrates a probe and sensor assembly for measuring the concentration or distribution of a vapor in a volume.

FIG. 1 illustrates a probe and sensor assembly 100 for measuring the concentration or distribution of a vapor in a volume. The probe and sensor assembly comprises a sensor 10 in communication with the gas passing through probe 14. In the embodiment shown in FIG. 1, the conduit 12 provides the gas communication path connecting the gas passing though probe 14 to the sensor 10. The sensor assembly may be portable or fixed. In the embodiments shown in FIG. 1, the probe 14 comprises a body 11 that includes inlets 16 to allow the vapor to enter an interior chamber 15 of the probe body 11 and travel down the conduit 12 to the sensor 10.

The gas sensor 10, which may also be referred to as a detector or measuring instrument, may be any suitable device that measures a physical quantity of a desired gas and converts it into a signal which can be read by an observer or by an instrument. This is typically done in the electronic domain and the sensor converts the concentration of the material or agent in the gas phase that the sensor encounters into an electronic signal, which may then be displayed or further read by a controller or other processor.

The gas sensor 10 may be designed to detect any type of gas including combustible gases, flammable and toxic gases, oxygen or oxygen depletion, carbon dioxide, helium, hydrocarbons, Halon 1301, Halon Replacements, or other volatile organic compounds. In a preferred embodiment, the sensor is designed to detect one or more Halon Replacements that may be used as a fire retardant.

In a preferred embodiment, probe and sensor assembly 100 communicates with a control system via electrical leads (not shown). However, in some embodiments probe and sensor assembly 100 may communicate with a control system wirelessly. Various protocols for wireless communication are well known in the art including WiFi, Bluetooth, and various other wireless protocols.

In the embodiment shown in FIG. 1, the probe and sensor assembly 100 includes a probe 14 that has an inner chamber 15 that is in communication with the conduit 12. In other embodiments, the probe and sensor assembly 100 may include a probe comprising a body that comprises a porous plug that fits in the end of the conduit 12 or, alternatively, the distal end of a cylindrical probe body piece so that the sensor 10 is in gas communication with gas passing through the probe. However, in a preferred embodiment, the sensor probe assembly 100 includes an additional probe 14.

The probe 14 may be made of any suitable material, but in a preferred embodiment the gas probe is made of a material such as stainless steel. In other embodiments other metals may be used such as nickel, brass, copper, steel or others. In yet other embodiments, other materials, including, for example, plastic, rubber, and ceramic may be used. At a minimum, the material used for the probe 14 should be a material that does not react with the gas being sampled. The gas probe 14 may be an important interface between the sensor 10 and the environment. In some embodiments, the sensor 10 may actually be small enough to fit within or be directly coupled to the probe 14. In such compact embodiments, only electrical leads may need to come from the probe 14/sensor 10 combination, and the conduit 12 interface between the probe 14 and the sensor 10 may be effectively eliminated.

In the embodiment shown in FIG. 1, the body 11 of probe 14 comprises a plurality of inlets 16. The gas in the environment may enter the probe 14 through the inlets 16. The gas is then channeled down the conduit 12 to the sensor 10 where the gas is analyzed.

Although in the embodiment shown in FIG. 1 only three inlets are shown on the probe 14, the probe 14 may include any number of inlets 16 and the inlets 16 may be placed in any suitable location on the probe including but not limited to on the sides, top, or tip of the probe. In a preferred embodiment, the body 11 of the probe is made of a porous material 18 such that tens, hundreds, or even thousands of miniature inlets 16 exist. In an even more preferred embodiment, the paths formed by the inlets are preferably tortuous such that the air/agent mixture being drawn into the probe must follow a convoluted or tortuous path to pass through the body 11 of the probe 14.

Figure 2:
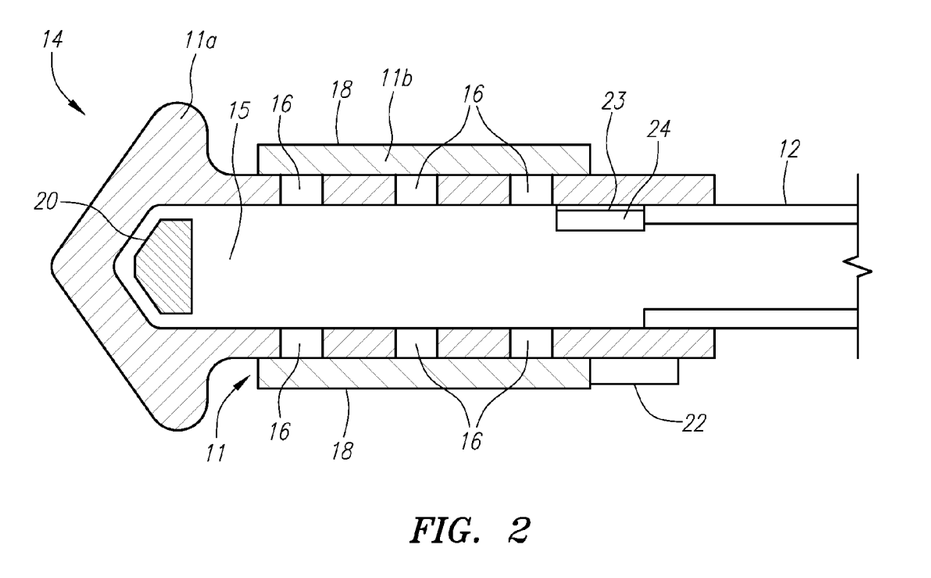
FIG. 2 illustrates a cross section of one embodiment of a probe that may be used in the probe and sensor assembly of FIG. 1 to measure concentrations of materials that exist in both the liquid and gas phase.

FIG. 2 illustrates a cross section of one embodiment of a probe 14 that may be used, for example, in the probe and sensor assembly of FIG. 1 to measure concentrations of materials that exist in both the liquid and gas phase. As may be seen in FIG. 2, the probe 14 comprises a body 11 that comprises a main body component 11a and a cylindrical sleeve 11b disposed around the main body component 11a. In the present embodiment, the cylindrical sleeve 11b is formed from the porous material 18. As a result, the probe 14 shown in FIG. 2 comprises a probe body 11 that includes an inner chamber 15 and comprises a porous material 18. In addition, the probe 14 comprises a heating unit 20 in thermal communication with the porous material 18. The porous material 18 defines a plurality of gas passageways in communication with atmosphere on one end and with the inner chamber 15 on their other end. Moreover, the porous material 18, which covers inlets 16 provided in the main body component 11a, is designed to capture the liquid phase droplets of the agent while the heating element 20 is designed to heat the probe 14 sufficiently to vaporize the captured liquid phase droplets into a gas. By designing a probe 14 capable of vaporizing the liquid phase droplets of an agent, conventional gas sensor equipment that is only capable of measuring agents in the gas phase may be used for sensor 10.

The porous material 18 may be any suitable material that has a pore size that helps capture the liquid phase droplets and suspends them for a sufficient time to allow the droplets to be vaporized by the heated probe while allowing the gas being sampled to pass therethrough. In a preferred embodiment, the porous material 18 is thermally conductive such that it is also heated and helps vaporize the liquid droplets of the agent. In some embodiments, the material may be a metal such as iron, titanium, steel, nickel, aluminum or various other metals. In other embodiments, the porous material may be a ceramic.

The porous material 18 may be positioned on the main body component 11*a* of probe 14 in a number of different ways. The embodiment shown in FIG. 2 shows the porous material 18 forming a sleeve 11*b* disposed around the main body component 11*a* of probe 14 and covering the inlets 16. However, in other embodiments, the porous material 18 may simply be inserted in the inlets 16. The porous material 18 may be located in various different positions as long as the porous material 18 sufficiently obstructs the inlets 16 such that the liquid phase droplets are suspended on the probe 14 long enough to vaporize. In a preferred embodiment, such as the embodiment described in connection with FIG. 4, the entire body 50 of the probe 14 is made from a porous material 18.

In the preferred embodiment, the heating element 20 is designed to provide the necessary heat to vaporize the agent as it passes through the porous material 18 and enters the inner chamber 15. Probe heating elements 20 are well known in the art and the probe heating element 20 may be any type of heating unit including those commonly known. In some embodiments, the heating element 20 uses electrical resistance to generate heat. In other embodiments, the heating element 20 may use other techniques to generate the necessary heat.

In the embodiment shown in FIG. 2, the heating element 20 is placed in conductive communication with the end of the probe 14 such that the heat transfers into the end of the probe 14 and is then conducted throughout the probe by the conductive nature of the material of the probe 14. However, in other embodiments, the heating element 20 may be located in other locations including within the porous material 18 or outside the probe 14. In many embodiments, the heat from the heating element 20 may be conducted into the porous material 18 through the body 11 of the probe 14, however, in other embodiments, the heating element 20 may be in direct thermal communication with the porous material 18.

In some embodiments, the probe 14 may also include a thermal sensor 24, an insulator 23, and an anemometer 22. The thermal sensor 24 may be any type of thermal sensor including but not limited to various different types of thermocouples, thermistors, or resistance thermocouple devices. In a preferred embodiment, both the thermal sensor 24 and the heating element 20 are coupled together through a controller (not shown) so that the heating element 20 may be controlled based on feedback from the thermal sensor 24 in a closed loop configuration. The controller may be implemented in hardware or software by any of the well known techniques. By controlling the heating element 20 based on the feedback from the thermal sensor 24, the air temperature of the air/agent mixture passing through the probe may be controlled and accordingly, the proper temperature to vaporize the agent may be more precisely maintained. Along with insuring vaporization, the feedback loop may also be used to prevent overheating.

To this end, in a preferred embodiment, the thermal sensor 24 is positioned and insulated sufficiently to best measure the temperature of the air as it passes through the porous material 18. In the embodiment shown in FIG. 2, the thermal sensor is insulated from the body 11 of the probe 14 with an insulator 23. The insulator 23 may be constructed from any well known thermal insulating material or combination of materials.

The anemometer 22 may be any type of well known anemometer. In a preferred embodiment, the anemometer 22 is a hot wire anemometer. However, other types of anemometers may be used. The feedback from the anemometer is used to calculate the velocity of the air travelling past the probe 14. In a preferred embodiment, the velocity of the air that traverses the probe 14 may be used to calculate the concentration of an agent in both the gas and liquid form because the portion of the agent in the liquid phase will be converted to gas and consumed by the probe 14. In a preferred embodiment, the air velocity and temperature are used to correlate the measurement on a mass basis by calculating a local mass flow.

In different embodiments, the anemometer 22 may be located in various different locations, however, in the preferred embodiment, the anemometer 22 is located on the outside of the probe near the inlets 16. Positioning the anemometer 22 on the outside of the body 11 of probe 14 is advantageous because it gives the anemometer 22 a good position from which to measure the velocity of the air passing by or through the body 11 of probe 14. In some embodiments, the anemometer 22 may be integrated into the porous material 18 such that it measures the velocity of the air passing through the porous material. In a preferred embodiment, the anemometer 22 is located on the surface of the porous material 18 just above an inlet 16 or just under the surface thereof. In some embodiments, an anemometer 22 is not used.

In operation, the probe of FIG. 2 is placed in an environment where it is desirable to know the concentration of an agent that exists in both the gas and liquid form i.e. a "fog mist." Gas mixture and droplets permeate through the porous material 18 where the heat from the heating unit 20 vaporizes the droplets into a gas and the now gas/gas mixture continues into the interior chamber 15 of the probe 14. The mixture is channeled down the conduit 12 to the sensor 10. During the process, a controller may monitor the temperature of the incoming air using the thermal sensor 24. The input from the thermal sensor may be used to control the temperature of the heating unit 20 in a feedback loop. At the same time, the anemometer 22 may measure the velocity of the air and provide it as data to be used in the concentration calculation.

In some embodiments, the lack of a positive pressure is used to transfer the gas mixture down the inner chamber 15 or down the conduit 12 towards the sensor 10. In other embodiments, a slight vacuum may be pulled to draw the sampled air through the body 11 of probe 14 and then down the inner chamber 15 and the conduit 12 and towards the sensor 10. In practice, pulling this type of vacuum may also help draw the air in from outside the probe 14 through the porous material 18 and into the inner chamber 15 of the probe 14.

Figure 3:
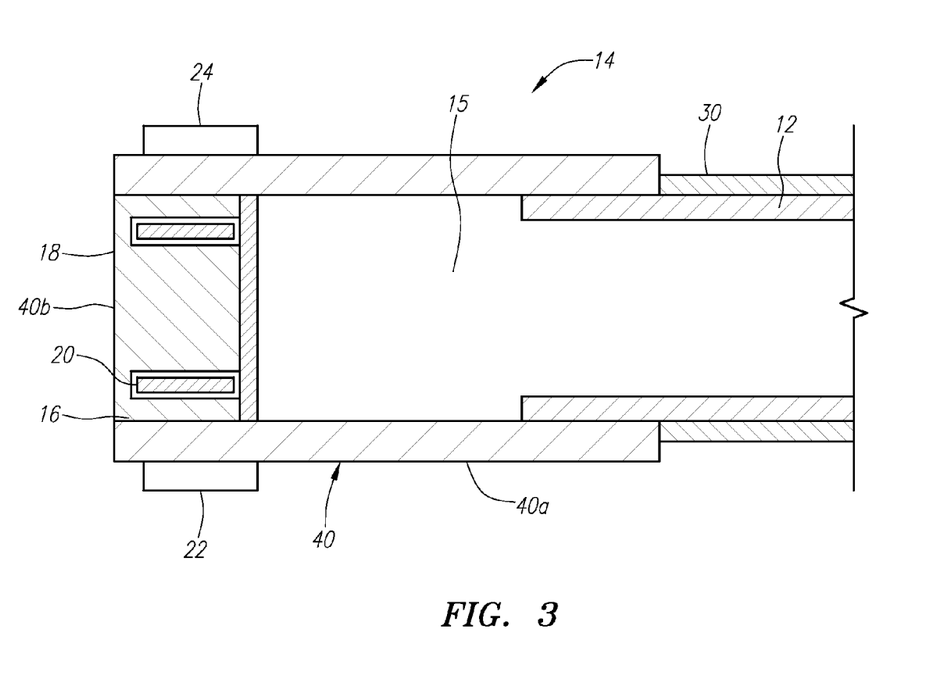
FIG. 3 illustrates a cross section of another embodiment of a probe for use in measuring concentrations of materials that exist in both the liquid and gas phase.

When the probe 14 of the embodiment shown in FIG. 2 is used in a probe and sensor assembly 100, a thermal conditioning element 30 may be disposed around conduit 12 in the manner illustrated in FIG. 3. The thermal conditioning element 30 is designed to condition the temperature of the conduit 12 such that the already vaporized agent does not condense on the conduit 12 on the way to the sensor 10. The thermal conditioning element 30 is designed to prevent an agent dew point effect between the probe 14 and the sensor 10.

In various different embodiments, thermal conditioning element 30 may be passive or active. For example, in one embodiment, thermal conditioning element 30 may be insulation designed to maintain the heat within the conduit 12. In other embodiments, the thermal conditioning element 30 may be active and provide heat through resistive heating or other active heating techniques. In a preferred embodiment, the thermal conditioning element 30 may extend the length of the conduit 12. However, in other embodiments, the thermal conditioning element 30 may only cover a portion of conduit 12.

FIG. 3 illustrates a cross section of another embodiment of a probe 14 for use in measuring concentrations of materials that exist in both the liquid and gas phase. The embodiment shown in FIG. 3 includes elements similar to that of the embodiment shown in FIG. 2 but arranged differently. For example, the embodiment of the probe 14 shown in FIG. 3 comprises a body 40 comprising a first cylindrical element 40a and a plug 40b disposed in the distal end of the cylindrical element 40a. In addition, in the embodiment shown in FIG. 3, the plug 40b is formed from the porous material 18, and the heating element 20 is contained within the plug 40b and is ring shaped.

In the embodiment shown in FIG. 3, anemometer 22 and thermal sensor 24 are located outside on the exterior of the body 40 of the probe 14. In the embodiment shown in FIG. 3, no specific insulation is needed for thermal sensor 24 because the body 40 of the probe may be designed from a non-conducting material due to the location of the heating element 20 within the porous material 18. However, in other embodiments, the thermal sensor 24 may be further insulated to ensure no heat transfer from the body 40 of the probe 14.

In operation, the embodiment of FIG. 3 operates similar to the embodiment shown in FIG. 2 except the gas/liquid mixture enters the probe 14 from the tip. The porous material is thermally heated from within by the heating element 20, which causes any liquid phase agent coming in contact with the porous material 18 to vaporize. Similar to the embodiment shown in FIG. 2, the gas/gas mixture may then be guided down the conduit 12 towards the sensor 10.

As may be seen in both FIG. 2 and FIG. 3, the probes 14 may be attached to a conduit 12 in a probe and sensor assembly 100. In a preferred embodiment, the implementation of FIG. 2 and FIG. 3 may be accomplished by retrofitting existing probes. In other embodiments, new probes may be constructed according to the teachings herein and fit to the conduit 12 of existing probe and sensor systems 100.

In a preferred embodiment the porous material 18 may be formed by sintering. Sintering allows unique geometries to be formed and preferably porous material 18 has a unique geometry. In a preferred embodiment, the unique geometries a plurality of convoluted paths defining a plurality of tortuous gas passageways extending from the exterior surface of the probe body 40 to the inner chamber 15 of the probe body 40. For example, porous material 18 may be constructed from a plurality of tiny spherical particles all stuck together by, for example, sintering. Such a construction would create a plurality of tortuous gas passageways for the gas to pass through.

Figure 4A:
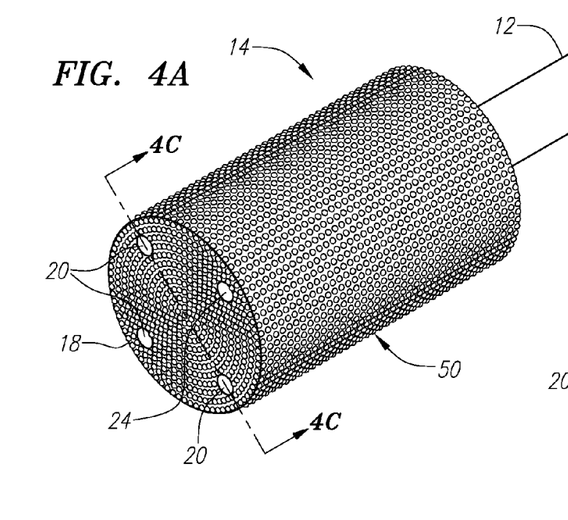
FIG. 4A illustrates a perspective view of yet another embodiment of a probe for use in a measuring concentrations of materials that exist in both liquid and gas phase.

FIG. 4A illustrates a perspective view of one embodiment of a probe 14 for use in a measuring concentrations of materials that exist in both liquid and gas phase. In the embodiment shown in FIG. 4A, the entire body 50 of probe 14 is made out of a porous material 18. In the embodiment of FIG. 4A, the porous material 18 creates thousands of inlets or paths between the exterior and the interior of the probe 14. The convoluted paths help ensure that any liquid phase agent that comes in contact with the body 50 of probe 14 is converted into gas prior to passing into the interior of the probe 14. A tortuous path may be any path with multiple turns. However, in a preferred embodiment, a tortuous path includes numerous turns and small spaces typical of a sintered metal filters or metal sponge materials.

In the embodiment shown in FIG. 4A, four cylindrical holes are provided in the end of the probe 14. The four cylindrical holes allow the insertion of thermal sensors 24, anemometers 22, or heating elements 20. In various embodiments, various configurations of thermal sensors 24, anemometers 22, and heating elements 20 may be used. In the embodiment shown in FIG. 4A, three (3) heating elements 20 and one (1) thermal sensor are used. In the embodiment of FIG. 4A, the heating elements 20 directly heat the porous material 18 and the thermal sensor 24, directly senses the temperature of the porous material 18.

Figure 4B:
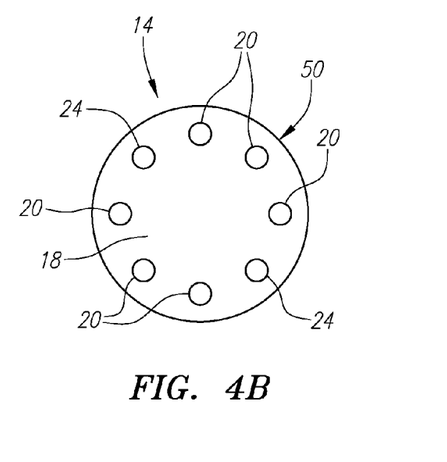
FIG. 4B illustrates an end view of the probe shown in FIG. 4A.

FIG. 4B illustrates an end view of yet another embodiment of a probe 14 for use in measuring concentrations of materials that exist in both liquid and gas phase. In the embodiment shown in FIG. 4B, numerous heating elements and sensors are located in cylindrical holes provided in the distal end of the probe body 50 formed from porous material 18. In various embodiments, any number of thermal sensors 24, heating elements 20 or anemometers 22 may be used.

Figure 4C:
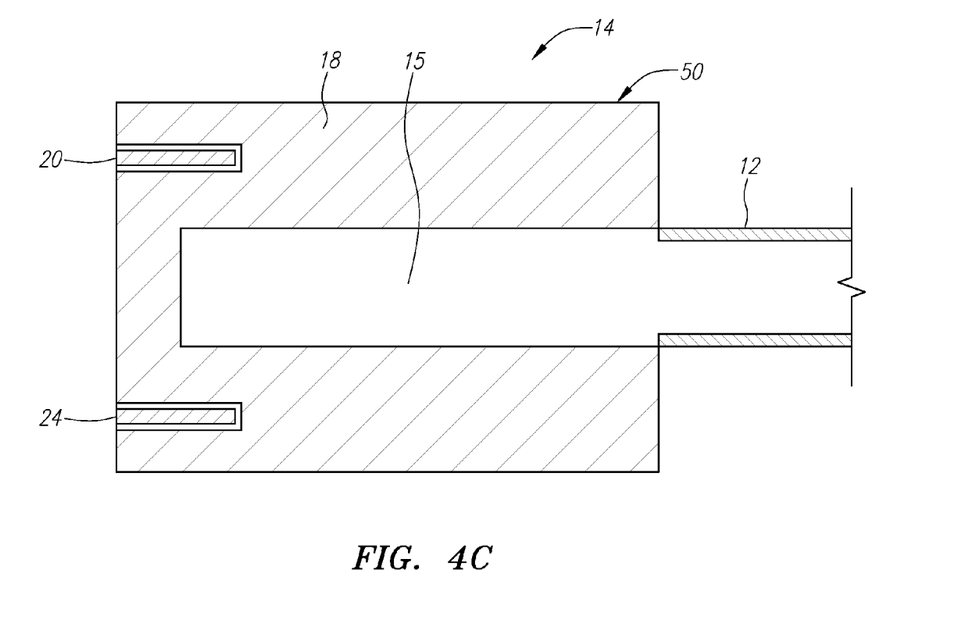
FIG. 4C illustrates a cross sectional view of the probe shown in FIG. 4A.

FIG. 4C illustrates a cross sectional through the t probe 14 of FIG. 4A. In the embodiment shown in FIG. 4A, the porous material 18, creates thousands of tortuous gas passageways extending from the exterior surface of the body 50 of probe 14 to the inner chamber 15 of the probe 14.

The unique geometry of the porous material 18 may serve several valuable functions. The unique geometry may help the probe heat low temperature air and vaporize drops of liquid phase agent transported by the air. The geometry of porous material 18 may further assist in integrating the vaporized agent into the air as it passes through into the inner chamber 15 of the probe. A more evenly distributed or integrated vaporized agent will help give more consistent readings by the sensor 10.

In a preferred embodiment, the geometry of the porous material 18 is designed to have air flow properties that maintain a zero pressure disturbance between the probe 14 and sensor 10. This is necessary to prevent measurement offset due to change in sonic velocity at each sensor.

Figure 5:
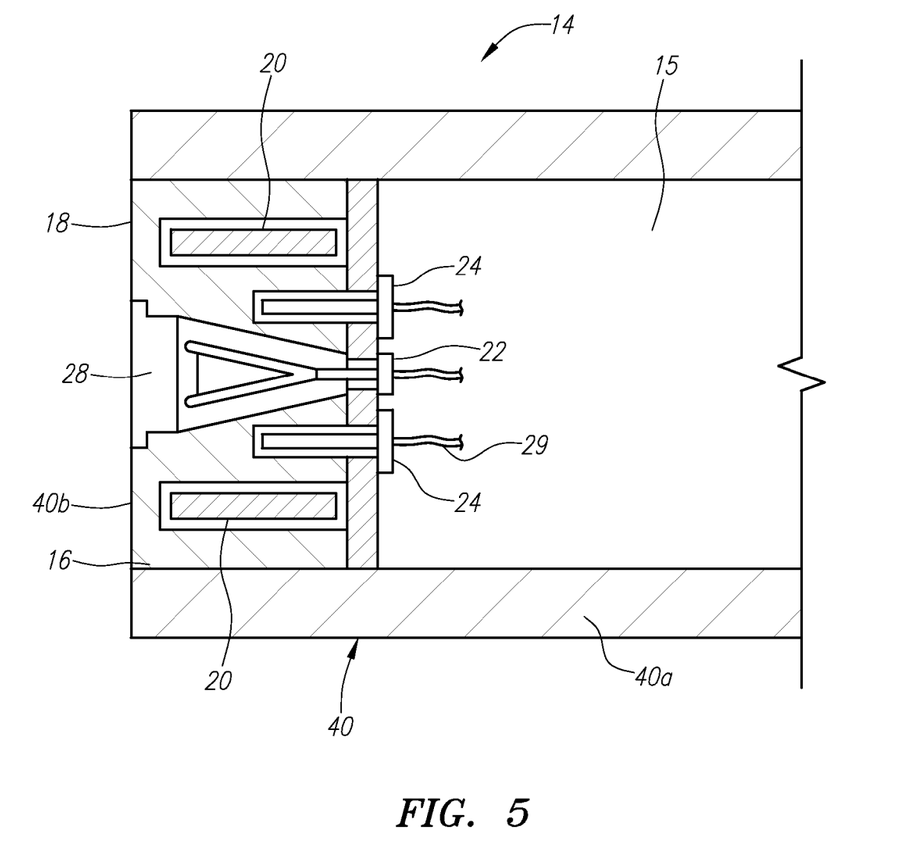
FIG. 5 illustrates a cross section of still another embodiment of a probe for use in measuring concentrations of materials that exist in both the liquid and gas phase.

FIG. 5 illustrates a cross section of still another embodiment of a probe 14 for use in measuring concentrations of materials that exist in both the liquid and gas phase. The embodiment shown in FIG. 5 is similar to the probe tip in FIG. 3, except in FIG. 5, the thermal sensors 24 and anemometer 22 are also integrated into the porous material 18 in addition to the heating element 20. In the embodiment shown, more than one thermal sensor 24 is used.

As shown in FIG. 5, the thermal sensors 24 interface with the proximal end of the porous material 18 (or plug 40b) using a flange configuration. In other embodiments, other mating techniques may be used. The porous material 18 also includes a recessed area 28 formed in the distal end of the plug 40b to allow the hot-wire anemometer 22 to be loaded from the distal side. In other embodiments, the hot-wire anemometer 22 may be integrated into the porous material 18 in other configurations. Sensor leads 29 are also shown in FIG. 5 for reference. In the preferred embodiments, the sensors transfer their information to a control unit via leads 29. However, in other embodiments, the data may be transferred to a controller wirelessly.

Figure 6:
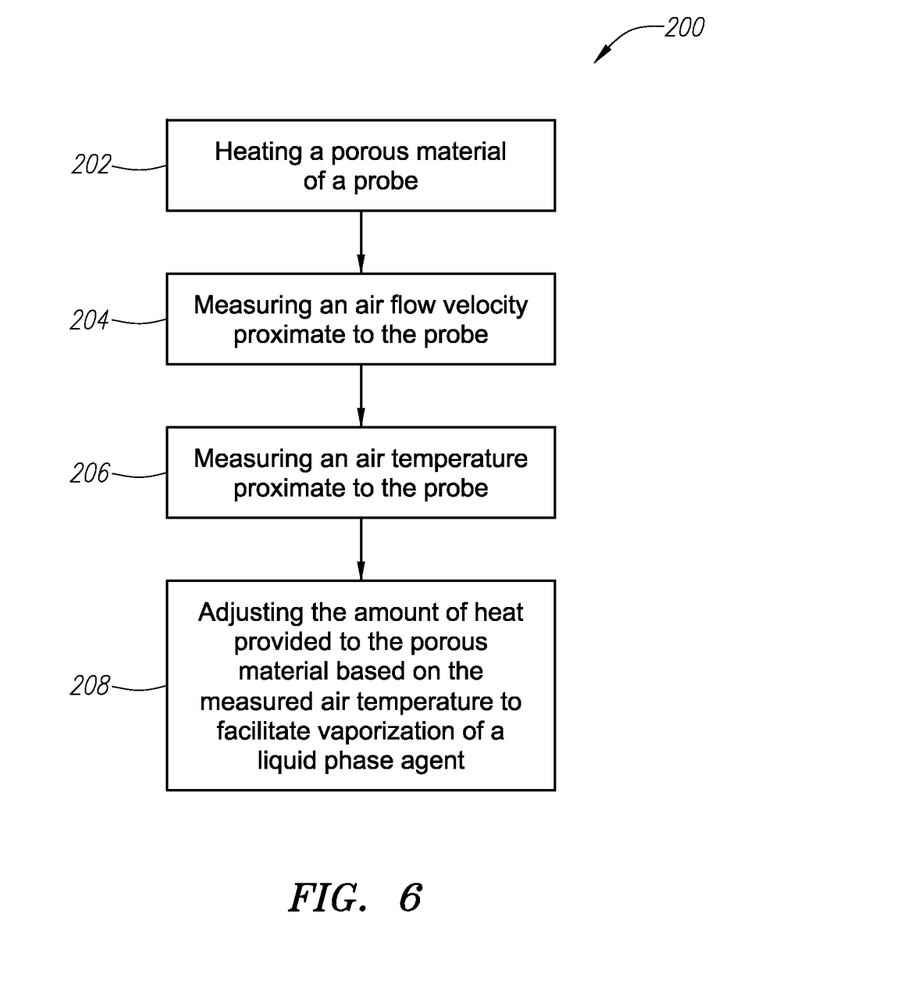
FIG. 6 illustrates one embodiment of a novel method for measuring the concentration of an agent that exists in both the gas and liquid form within a volume.

FIG. 6 illustrates one embodiment of a novel method 200 for measuring the concentration of an agent that exists in both the gas and liquid form within a volume. In step 202, the porous material 18 of a probe 14 is heated. Any method of heating may be used and any of the various probe designs described above may be used. In addition, the heat may be applied directly to the porous material or the porous material may be heated through contact and conduction with another portion of the probe that is being heated.

In step 204, the air flow velocity proximate to the probe is measured. In various different embodiments, the air flow velocity may be measured within the probe, external to the probe, within an inlet or within the porous material. In a single embodiment, the airflow may be measured in multiple locations. In the preferred embodiment, the air flow velocity is measured within the porous material very close to the surface. The air flow velocity may be measured with an anemometer or any other type of sensor suitable for measuring the velocity of a gas. In a preferred embodiment a hot-wire anemometer is used.

In step 206, the air temperature proximate to the probe is measured. In various different embodiments, the air temperature may be measured inside the probe, outside the probe, within the inlet, or within the porous material. In some embodiments, the air temperature may be measured in multiple locations. In some embodiments, the air temperature may be measured by taking the measurement of the probe itself and making a correlation to the air temperature. For example, a system may measure the temperature of the porous material 18 instead of the actual air and then correlate the temperature of the porous material 18 to the air temperature surrounding the porous material 18. Similarly, in other embodiments, the temperature of any other suitable portion of the probe 14 may be used and correlated to air temperature.

In step 208, the temperature measured in step 206 may be used to provide feedback to a heating element to facilitate vaporization of a liquid phase agent. In step 208, the amount of heat provide to the porous material 18 may be controlled to facilitate vaporization. In a preferred embodiment, step 208 optimizes vaporization while preventing overheating.

Figure 7:
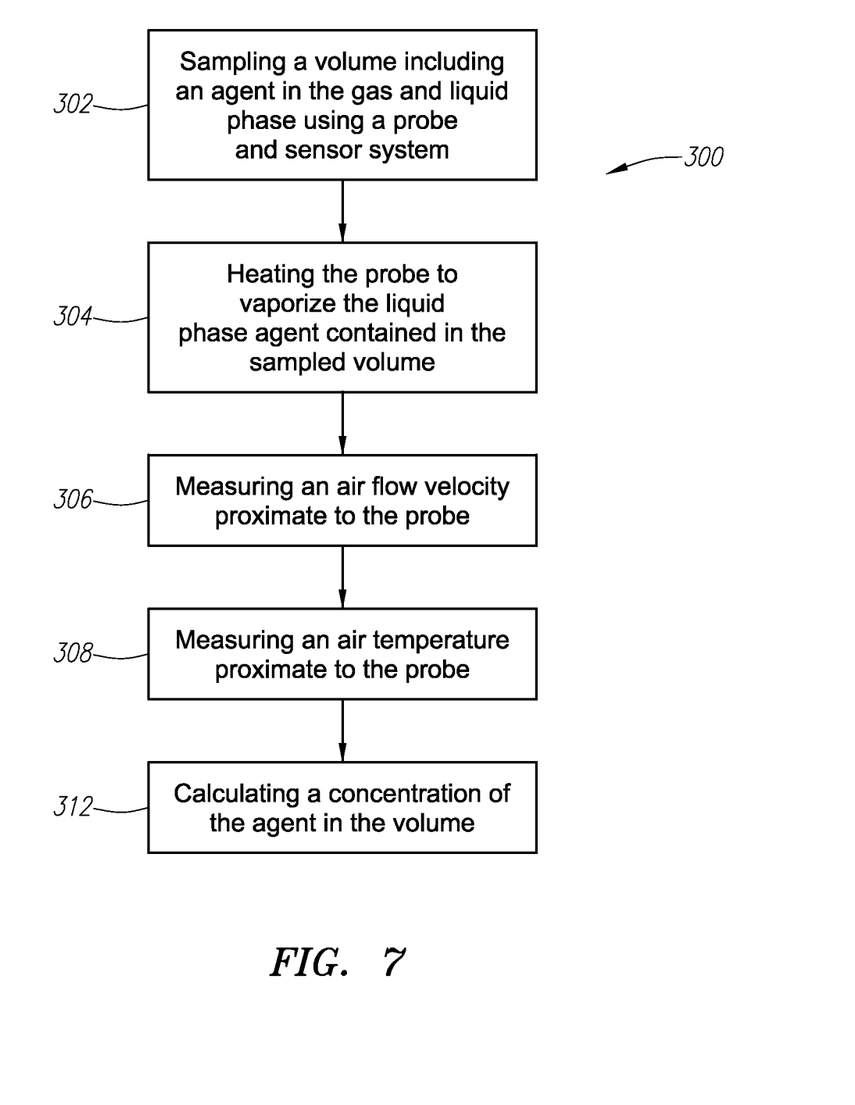
FIG. 7 illustrates an embodiment of a novel method for calculating a concentration of an agent existing in both a liquid and gas form in a volume.

FIG. 7 illustrates an embodiment of a novel method for calculating a concentration of an agent existing in both a liquid and gas form in a volume. In step 302 of the embodiment shown in FIG. 7, a probe 14 is used to sample a volume for an agent that exists in both the liquid and gas phase. In step 304 the probe is heated to vaporize the liquid phase of the agent. In the preferred embodiment, a substantial amount, 85% or greater, of the liquid phase is vaporized. In an even more preferable embodiment, 95% or more of the liquid phase is vaporized. In a yet even more preferable embodiment, 99% or more of the liquid phase is vaporized.

In steps 306 and 308 the air flow and temperature are measured respectively. The concentration of the agent in the volume is then calculated in step 312.

Although the embodiments have been described with reference to preferred configurations and specific examples, it will readily be appreciated by those skilled in the art that many modifications and adaptations of the probes and probe sensor systems, and methods of using probes described herein are possible without departure from the spirit and scope of the embodiments as claimed hereinafter. Thus, it is to be clearly understood that this description is made only by way of example and not as a limitation on the scope of the embodiments as claimed below.

What is claimed is:

1. A probe for use in measuring an agent in gas and liquid form comprising: an outer body including a void inner chamber, wherein the outer body comprises hundreds of paths leading from inlets on the exterior surface of the outer body to the void inner chamber and wherein the outer body is formed from a sintered material; a heating element in thermal communication with the outer body; and a thermal sensor in thermal communication with the outer body.

2. The probe of claim 1, further comprising an anemometer located proximate to the inlets.

3. The probe of claim 1, wherein the heating element is located within the outer body.

4. The probe of claim 2, wherein the anemometer is located within the outer body.

5. The probe of claim 1, wherein the thermal sensor is located within the outer body.

6. The probe of claim 1, further comprising a conduit in communication with the inner chamber and a thermal conditioning element designed to condition the temperature of the conduit to avoid condensation of the agent.

7. The probe of claim 1, wherein the agent is a fire retardant.

8. A method of measuring the concentration of an agent in gas and liquid form comprising the steps of:
heating a probe comprising a sintered outer body with an inner chamber, the sintered outer body comprising hundreds of paths from inlets on an exterior surface of the outer body to the inner chamber;
measuring an air temperature proximate to the probe; and
adjusting the heat added in the heating step based on the measured air temperature in order to facilitate vaporization of a liquid phase agent.

9. The method of claim 8, further comprising the step of measuring the air velocity proximate to the probe.

10. The method of claim 8, wherein the probe includes a thermal sensor and anemometer located within the outer body.

11. The method of claim 8, further comprising the step of calculating a mass flow rate of the agent.

12. The method of claim 11, further comprising the step of calculating the concentration of the agent in the volume.

13. The method of claim 8, wherein the agent is a fire retardant.

14. The method of claim 13, wherein the fire retardant is FK-5-1-12.

15. A probe comprising:
   an outer body comprising a sintered material;
   an inner chamber extending from one side of the outer body through the outer body to a bottom proximate an opposite side of the outer body;
   a plurality of tortuous paths that extend through the outer body from an external surface of the outer body to the inner chamber;
   a thermal sensor located within the outer body; and
   an anemometer located within the outer body.

16. The probe of claim 15, further comprising a heating element in thermal communication with the outer body.

17. The probe of claim 15, further comprising a conduit in communication with the probe and coupled to a thermal conditioning element designed to prevent condensation of the agent.

18. The probe of claim 16, wherein the heating element is located within the outer body.

19. A probe and sensor assembly for measuring an agent in gas and liquid form comprising:
   a probe according to claim 1 or claim 15, wherein the paths define a plurality of gas passageways sized to permit the agent in the gas phase to pass there through; and
   a gas sensor in gas communication with a downstream side of the plurality of gas passageways.

20. A probe and sensor assembly according to claim 19, wherein the gas sensor is in gas communication with the downstream side of the gas passageways via a conduit interposed between the probe and gas sensor.

21. A probe and sensor assembly according to claim 20, further comprising a thermally conditioning element in thermal communication with at least a portion of the conduit, the thermally conditioning element designed to condition the temperature of the conduit to avoid condensation of the agent within the conduit.

22. A probe and sensor assembly according to claim 20, wherein the thermal conditioning element is an active thermal conditioning element.

* * * * *